US009895350B2

(12) United States Patent
Bodor et al.

(10) Patent No.: US 9,895,350 B2
(45) Date of Patent: *Feb. 20, 2018

(54) METHOD OF DOSING AND USE OF SOFT ANTICHOLINERGIC ESTERS

(71) Applicant: BODOR LABORATORIES, INC., Miami, FL (US)

(72) Inventors: Nicholas S. Bodor, Bal Harbour, FL (US); David Angulo, Coral Gables, FL (US)

(73) Assignee: BODOR LABORATORIES, INC., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/200,129

(22) Filed: Jul. 1, 2016

(65) Prior Publication Data

US 2016/0310464 A1 Oct. 27, 2016

Related U.S. Application Data

(63) Continuation of application No. 14/941,183, filed on Nov. 13, 2015, now Pat. No. 9,492,429, which is a continuation of application No. 14/213,242, filed on Mar. 14, 2014, now Pat. No. 9,220,707.

(60) Provisional application No. 61/798,073, filed on Mar. 15, 2013.

(51) Int. Cl.
*A61K 8/00* (2006.01)
*A61K 31/40* (2006.01)
*A61K 8/49* (2006.01)
*A61Q 15/00* (2006.01)
*A61K 9/00* (2006.01)
*A61K 47/10* (2017.01)
*A61K 8/41* (2006.01)
*A61K 31/4015* (2006.01)
*A61K 31/14* (2006.01)
*A61K 31/205* (2006.01)

(52) U.S. Cl.
CPC ............ *A61K 31/40* (2013.01); *A61K 8/4913* (2013.01); *A61K 9/0014* (2013.01); *A61K 47/10* (2013.01); *A61Q 15/00* (2013.01); *A61K 8/416* (2013.01); *A61K 31/14* (2013.01); *A61K 31/205* (2013.01); *A61K 31/4015* (2013.01)

(58) Field of Classification Search
CPC ...... A61K 8/416; A61K 31/14; A61K 31/205; A61K 31/4015
USPC .................................. 424/65; 514/424, 947
See application file for complete search history.

(56) References Cited

U.S. PATENT DOCUMENTS 5,292,530 A   3/1994   McCrea
7,399,861 B2  7/2008   Bodor
7,417,147 B2  8/2008   Bodor
7,538,219 B2  5/2009   Bodor
7,576,210 B2  8/2009   Bodor
8,071,639 B2  12/2011  Bodor
8,147,809 B2  4/2012   Bodor
8,153,669 B2  4/2012   Press
8,383,625 B2  2/2013   Press
8,568,699 B2  10/2013  Bodor
8,618,160 B2  12/2013  Johnston et al.
8,628,759 B2* 1/2014   Bodor .................. C07D 207/10
                                                 424/65
8,679,524 B2  3/2014   Wassenaar
9,220,707 B2* 12/2015  Bodor .................. A61K 8/4913
9,492,429 B2* 11/2016  Bodor .................. A61K 8/4913
2003/0064040 A1  4/2003   Lukacsko
2006/0210504 A1  9/2006   Lukacsko
2009/0227590 A1  9/2009   Press
2009/0263341 A1  10/2009  Bodor
2009/0291960 A1  11/2009  Press
2012/0237573 A1  9/2012   Wassenaar

FOREIGN PATENT DOCUMENTS

JP    2009515889 A    4/2009
WO    2007/058971 A2  5/2007
WO    2009/051818 A1  4/2009

OTHER PUBLICATIONS

Ji, F., Wu, W-M and Bodor, N., "Studies on a soft glycopyrrolate analog, SG-1" Pharmazie, 2002, pp. 138-141, 2-5, vol. 57, No. 2, Govi-Verlag, Germany.
"Glycopyrronium bromide" downloaded at Wikipedia, http://en.wikipedia.org/wiki/Glycopyrronium_bromide on May 1, 2015.
Ji F., et al., "Synthesis and Pharmacological Effects of New N-Substituted Soft Anticholinergics Based on Glycopyrrolate," J. Pharmacy and Pharmacology, vol. 57, No. 11, Nov. 1, 2005, pp. 1427-1435, John Wiley & Sons Ltd. London, GB (pub.).
Wu, W.M. et al. "Stereoisomers of N-Substituted Soft Anticholinergics and Zwitterion Metabolite Based on Glycopyrrolate—Syntheses and Pharmacological Evaluations," Die Pharmazie, Mar. 2008, vol. 63, No. 3, pp. 200-209.

(Continued)

*Primary Examiner* — Kevin E Weddington
(74) *Attorney, Agent, or Firm* — Dentons US LLP

(57) ABSTRACT

A method of treating hyperhidrosis in a mammalian subject including: a) providing a composition including a pharmaceutically acceptable vehicle and from about 1.0% to about 25% of a compound having the formula:

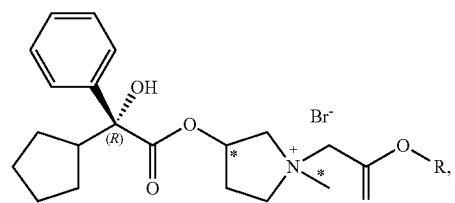

and b) topically administering the composition to skin of an area of a mammalian subject suffering from hyperhidosis, before bedtime, such that, compared to untreated, baseline conditions, sweat production is reduced by at least about 25% for at least about six (6) hours.

32 Claims, No Drawings

(56) References Cited

OTHER PUBLICATIONS

International Search Report and Written Opinion dated Jun. 18, 2015 for International Application No. PCT/US2015/020253, 9 pages, corresponding to related U.S. Appl. No. 14/285,488.
International Search Report and Written Opinion dated Jul. 17, 2014 for corresponding International Application No. PCT/US2014/028332, 12 pages.
Office Action dated Sep. 17, 2014 for related U.S. Appl. No. 141285,488.
Office Action dated Jan. 22, 2015 for related U.S. Appl. No. 14/285,488.
Office Action dated Feb. 4, 2015 for parent U.S. Appl. No. 14/213,242.
Japanese Office Action issued for Japanese Patent Application No. 2016-502761 Feb. 22, 2017, 4 pages.
Chinese Office Action and English translation issued for Chinese Patent Application No. 201480015677.0 Dec. 12, 2016, 14 pages.

\* cited by examiner

METHOD OF DOSING AND USE OF SOFT ANTICHOLINERGIC ESTERS

CROSS-REFERENCE TO EARLIER APPLICATIONS

This application is a continuation of U.S. application Ser. No. 14/941,183, filed Nov. 13, 2015, which is a continuation of U.S. application Ser. No. 14/213,242, filed Mar. 14, 2014, now U.S. Pat. No. 9,220,707, which claims benefit of U.S. Provisional Application No. 61/798,073, filed Mar. 15, 2013.

BACKGROUND

Various anticholinergic compounds have been previously described but are not optimal.

Muscarinic receptor antagonists are frequently used therapeutic agents that inhibit the effects of acetylcholine by blocking its binding to muscarinic cholinergic receptors at neuroeffector sites on smooth muscle, cardiac muscle, and gland cells as well as in peripheral ganglia and in the central nervous system (CNS). However, their side effects, which can include dry mouth, photophobia, blurred vision, urinary hesitancy and retention, drowsiness, dizziness, restlessness, irritability, disorientation, hallucinations, tachycardia and cardiac arrhythmias, nausea, constipation, and severe allergic reactions, often limit their clinical use. Topical administration of anticholinergic agents to targeted areas, such as sweat glands, where the localized blockage of muscarinic receptors will be of clinical benefit would be a desirable therapeutic strategy. However currently used topical anticholinergics can exhibit unwanted systemic side effects which can limit the dosage that can be safely administered.

Glycopyrrolate is among the quaternary ammonium anticholinergics which have reduced CNS-related side effects as they cannot cross the blood-brain barrier; however, because glycopyrrolate is eliminated mainly as unchanged drug or active metabolite, its topical administration is often associated with common undesirable anticholinergic systemic side effects. To increase the therapeutic index of anticholinergics, the soft drug approach has been applied in a number of different designs starting from various lead compounds, but there is a need for yet other new soft anticholinergics with clinically meaningful biological activity. These novel muscarinic antagonists, just as all other soft drugs, are designed to elicit their intended pharmacological effect at the site of application, but to be quickly metabolized into their designed-in, inactive metabolite upon entering the systemic circulation and rapidly eliminated from the body, resulting in reduced systemic side effects and increased therapeutic index.

Soft anticholinergic zwitterions have been described in US Publication No. 2012/0141401, and its related patents, U.S. Pat. Nos. 8,071,693; 7,538,219; and 7,417,147. Soft anticholinergic esters have been described in US Publication No. 2012/0177590 and its related patents U.S. Pat. Nos. 8,147,809; 7,576,210; and 7,399,861. Although these published applications and patents identified the potential for the zwitterion or ester forms of anticholinergics to be used for treating hyperhidrosis, activity and duration of action are unexpectedly high, based on a comparison to published mydriasis data, was not known or previously described.

Each of the US Publication Nos. 2012/0141401 and 2012/0177590 and their related patents U.S. Pat. Nos. 8,147, 809; 8,071,693; 7,576,210; 7,538,219; 7,417,147; and 7,399,861 are hereby incorporated by reference in their entirety.

Hyperhidrosis is an idiopathic pathological condition characterized by excessive, uncontrollable sweating beyond that required to cool the body. A hyperfunction of the sweat glands and a disturbance of their cholinergic stimulation have been described as possible causes of this condition. It is known to affect approximately 3% of the population. Hyperhidrosis not only may result in intense social embarrassment, but also may even interfere with a person's occupation.

Hyperhidrosis most often involves one or several areas, especially the hands, axillae, feet or face, although it can even involve the whole body. Axillary hyperhidrosis is the most common form, followed by palmar hyperhidrosis. Antiperspirants alone are generally not effective in treating this excessive perspiration. Oral medications are occasionally beneficial, but may have side effects. Other therapeutic alternatives include surgical procedure such endoscopic thoracic sympathectomy. Although the surgery affords permanent benefit in some 40% to 90% of affected individuals, it is invasive, requires general anesthesia and is not without potential side effects. As many as 50% of persons who have undergone thoracic sympathectomy develop compensatory and annoying sweating of the trunk or thighs.

Botulinum A neurotoxin (BOTOX) which blocks the action on sweat glands of acetylcholine that is released by the autonomic nerves, has proven effective in hyperhidrosis. Minute amounts of BOTOX injected into the palms or axillae of affected individuals results in statistically significant benefit. The effect lasts for several months but requires repeated injections and is often not a suitable alternative for pediatric patients.

A non-invasive, convenient and effective treatment having high sweat reduction activity, long duration, and with fewer side effects would be a welcome alternative for treating hyperhidrosis.

Topical glycopyrrolate has been used previously to treat gustatory sweating associated with diabetic autonomic neuropathy. In this disorder, sweating that often is profuse, begins soon after the patient ingests food, starting on the forehead and then involving the face, scalp and neck. A solution of glycopyrrolate was applied to the face of the patient which prevented the gustatory sweating.

Similarly, glycopyrrolate has also been used previously to treat gustatory sweating associated with Frey's syndrome which may develop after parotidectomy. Frey's syndrome is believed to result from the aberrant re-innervation of the sweat glands of the face by the severed parotid parasympathetic nerve fibers.

In both diabetic gustatory sweating and Frey's syndrome, the profuse facial sweating is induced by the specific stimulus of eating. Moreover, the sweating in each is a consequence of a distinct neuropathological process. In contrast, hyperhidrosis occurs spontaneously without a specific stimulus.

This application is directed in part to the discovery that the daily topical application of a 5% concentration of a soft-anticholinergic compound to a mammal overcomes many of the prior problems in treating hyperhidrosis. In previous published mydriatic studies comparing soft-anticholinergic compounds to glycopyrrolate, comparable activity appears to have required as much as five times (5×) or more the concentration of the soft-anticholinergic compounds compared to glycopyrrolate. Surprisingly a compound as defined herein can provide clinically significant reduction of sweat production at a level of similar sweat reduction reported using comparable doses of glycopyrrolate, potentially making it a suitable treatment alternative for hyperhidrosis.

Additionally, there are provided advantages heretofore not achieved by conventional treatments for hyperhidrosis. For example, the soft-anticholinergic compound to be applied does not have the side effects associated with Botox treatments and may have an improved safety profile when compared to the systemic anticholinergic agents or topical glycopyrrolate.

SUMMARY

Methods of treating excessive sweating conditions in mammalian subjects, such as humans suffering from hyperhidrosis, are described using soft anticholinergic agents, and pharmaceutical compositions containing them are provided. The methods described relate to unexpected activity for the soft anticholinergic when administered topically before bedtime.

In one exemplary embodiment, there is provided a compound having the formula:

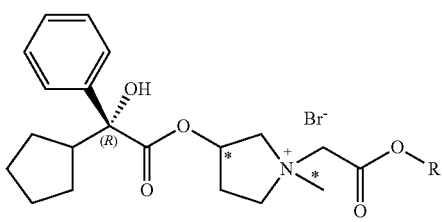

wherein R is methyl or ethyl, said compound having the R stereoisomeric configuration at the 2 position and the R, S, or RS steroisomeric configuration at the 1' and 3' position, or being a mixture thereof.

In other exemplary embodiments, there are provided pharmaceutical compositions comprising one or more of the compounds of the foregoing formula and pharmaceutically acceptable carriers therefor; pharmaceutical combinations comprising one or more of the compounds of the foregoing formula and another antiperspirant agent such aluminum chloride; and methods of using the subject compositions and combinations.

The compositions are preferably formulated for topical application in treatment, prevention, or amelioration of hyperhidrosis.

One preferred embodiment includes a method for treating, preventing, or ameliorating hyperhidrosis in a subject wherein the method comprises:
a) providing a composition comprising a pharmaceutically acceptable vehicle and from about 1.0% to about 25% of a compound having the formula:

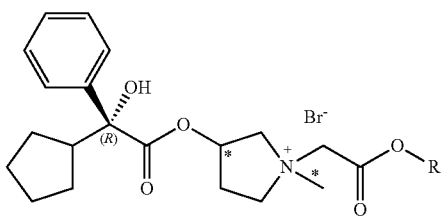

wherein R is methyl or ethyl, said compound having the R stereoisomeric configuration at the 2 position and the R, S, or RS steroisomeric configuration at the 1' and 3' position, or being a mixture thereof; and
b) topically administering before bedtime the composition to a subject suffering from hyperhidrosis, the topical administration being such that, compared to untreated, baseline conditions, sweat production is reduced for at least about six (6) hours by an amount which is unexpectedly substantially equivalent to an amount that sweat production is reduced, compared to untreated, baseline conditions, following administration of a composition comprising an equivalent concentration of glycopyrrolate.

In one embodiment, the method is carried out by administration of the composition to a human subject and can be applied to the skin of the subject at a superficial anatomic area in need of sweat reduction, preferably selected from a hand palm area, a foot plantar area, a groin area, an axilla area, and facial area of the subject.

The subject method can reduce sweat production by about 25% to about 99%, preferably by about 30% to about 75%, more preferably by about 45% to about 60%, and most preferably by about 50%, which can be a clinically significant endpoint for an indication for treating hyperhidrosis.

The method can employ the composition formulated as a solid or semi-solid, powder, gel, cream, lotion, foam, solution, suspension or emulsion, or the like and preferably comprises about 2% to about 10% concentration of the compound. One preferred embodiment employs the composition formulated as a 5% solution of the compound in 70% ethanol.

In addition, administration of a second dose, following the sleep cycle, within about 6-10 hours following the dose that preceded the sleep cycle, can also be a preferred method of administration or dosing regimen.

Surprisingly, the subject method can reduce sweat production from about 8 hours to about 24 hours, and preferably from about 8 hours to about 12 hours.

Another method concerns a novel dosing regimen whereby a subject suffering from hyperhidrosis is topically administered, before bedtime, a composition comprising a pharmaceutically acceptable vehicle and from about 1.0% to about 25% of a compound having the formula:

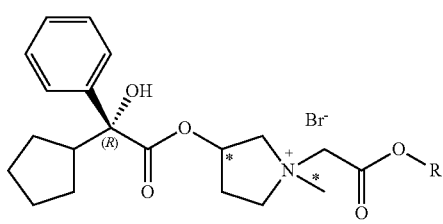

wherein R is methyl or ethyl, said compound having the R stereoisomeric configuration at the 2 position and the R, S, or RS steroisomeric configuration at the 1' and 3' position, or being a mixture thereof, such that, compared to untreated, baseline conditions, sweat production is reduced for at least about six (6) hours by at least about 25%, or which is a response substantially equivalent to an amount that sweat production is reduced, compared to untreated, baseline conditions, following administration of a composition comprising an equivalent concentration of glycopyrrolate.

The dosing regimen is preferably carried out by administration of the composition to a human subject and can be applied to the skin of the subject at a superficial anatomic area selected from a hand palm area, a foot plantar area, a groin area, an axilla area, and facial area of the subject.

The dosing regimen can reduce sweat production by about 25% to about 99%, preferably by about 30% to about 75%, more preferably by about 45% to about 60%, and most preferably by about 50%, which can be a clinically significant endpoint for an indication for treating hyperhidrosis.

The dosing regimen can employ the composition formulated as a solid or semi-solid, powder, gel, cream, lotion, foam, solution, suspension or emulsion, or the like and preferably comprises about 2% to about 10% concentration of the compound. One preferred embodiment employs the composition formulated as a 5% solution of the compound in 70% ethanol.

In addition, a dosing regimen can include a further step, after the first administration, comprising topically administering a second dose of the composition to the subject after the subject awakens. Surprisingly, the subject dosing regimen can reduce sweat production from about 8 hours to about 24 hours, and preferably from about 8 hours to about 12 hours.

DETAILED DESCRIPTION

Throughout this specification, the following definitions, general statements and illustrations are applicable:

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used herein, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a composition, the term "comprising" means that the composition includes at least the recited features or components, but may also include additional features or components.

The terms "consists essentially of" or "consisting essentially of" have a partially closed meaning, that is, they do not permit inclusion of steps or features or components which would substantially change the essential characteristics of a process or composition; for example, steps or features or components which would significantly interfere with the desired properties of the compounds or compositions described herein, i.e., the process or composition is limited to the specified steps or materials and those which do not materially affect the basic and novel characteristics of the invention.

The terms "consists of" and "consists" are closed terminology and allow only for the inclusion of the recited steps or features or components.

As used herein, the singular forms "a," "an" and "the" specifically also encompass the plural forms of the terms to which they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 20%.

As used herein, the recitation of a numerical range for a variable is intended to convey that the variable can be equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In the specification and claims, the singular forms include plural referents unless the context clearly dictates otherwise. As used herein, unless specifically indicated otherwise, the word "or" is used in the "inclusive" sense of "and/or" and not the "exclusive" sense of "either/or."

Technical and scientific terms used herein have the meaning commonly understood by one of skill in the art to which the application pertains, unless otherwise defined. Reference is made herein to various methodologies and materials known to those of skill in the art. Standard reference works setting forth the general principles of pharmacology include Goodman and Gilman's The Pharmacological Basis of Therapeutics, 10th Ed., McGraw Hill Companies Inc., New York (2001).

As used herein, "treating" means reducing, hindering or inhibiting the development of, controlling, inhibiting, alleviating and/or reversing the symptoms in the individual to which a composition comprising a compound as described above has been administered, as compared to the symptoms of an individual not being administered the compound or composition. A practitioner will appreciate that the combinations, compositions, dosage forms and methods described herein are to be used in concomitance with continuous clinical evaluations by a skilled practitioner (physician or veterinarian) to determine subsequent therapy. Such evaluation will aid and inform in evaluating whether to increase, reduce or continue a particular treatment dose, and/or to alter the mode of administration.

The compounds or compositions defined herein can also prevent the symptoms, or prevent the occurrence of the symptoms in the individual to which a composition comprising a compound as defined herein has been administered, as compared to the symptoms of an individual not being administered the compound or composition.

The methods described herein are intended for use with any mammalian subject/patient that may experience their benefits. Thus, the terms "subjects" as well as "patients," "individuals" and "warm-blooded animals" include humans as well as non-human subjects, such as animals that may experience hyperhidrosis.

Compounds as defined herein having the R configuration with respect to chiral center 2 are of particular interest.

Of particular interest are the compounds of the formula:

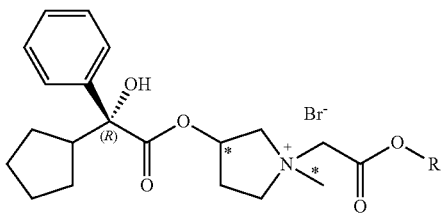

wherein R is methyl or ethyl, the compound having the R stereoisomeric configuration at the 2 position and the R, S, or RS steroisomeric configuration at the 1' and 3' position, or being a mixture thereof.

The following compounds are of particular interest:
(i) 3-(2-cyclopentyl-2-phenyl-2-hydroxyacetoxy)-1-(methoxycarbonylmethyl)-1-methylpyrrolidinium bromide;
(ii) 3-(2-cyclopentyl-2-phenyl-2-hydroxyacetoxy)-1-(ethoxycarbonylmethyl)-1-methylpyrrolidinium bromide;
(iii) (2R) 3-(2-cyclopentyl-2-phenyl-2-hydroxyacetoxy)-1-(methoxycarbonylmethyl)-1-methylpyrrolidinium bromide;
(iv) (2R) 3-(2-cyclopentyl-2-phenyl-2-hydroxyacetoxy)-1-(ethoxycarbonylmethyl)-1-methylpyrrolidinium bromide;
(v) (2R,3'R) 3-(2-cyclopentyl-2-phenyl-2-hydroxyacetoxy)-1-(methoxycarbonylmethyl)-1-methylpyrrolidinium bromide;
(vi) (2R,3'S) 3-(2-cyclopentyl-2-phenyl-2-hydroxyacetoxy)-1-(methoxycarbonylmethyl)-1-methylpyrrolidinium bromide;
(vii) (2R,3'R) 3-(2-cyclopentyl-2-phenyl-2-hydroxyacetoxy)-1-(ethoxycarbonylmethyl)-1-methylpyrrolidinium bromide;
(viii) (2R,3'S) 3-(2-cyclopentyl-2-phenyl-2-hydroxyacetoxy)-1-(ethoxycarbonylmethyl)-1-methylpyrrolidinium bromide;
(ix) (2R,1'R,3'S) 3-(2-cyclopentyl-2-phenyl-2-hydroxyacetoxy)-1-(ethoxycarbonylmethyl)-1-methylpyrrolidinium bromide;
(x) (2R,1'S,3'S) 3-(2-cyclopentyl-2-phenyl-2-hydroxyacetoxy)-1-(ethoxycarbonylmethyl)-1-methylpyrrolidinium bromide;
(xi) (2R,1'R,3'R) 3-(2-cyclopentyl-2-phenyl-2-hydroxyacetoxy)-1-(ethoxycarbonylmethyl)-1-methylpyrrolidinium bromide;
(xii) (2R,1'S,3'R) 3-(2-cyclopentyl-2-phenyl-2-hydroxyacetoxy)-1-(ethoxycarbonylmethyl)-1-methylpyrrolidinium bromide;
(xiii) (2R,1'R,3'S) 3-(2-cyclopentyl-2-phenyl-2-hydroxyacetoxy)-1-(methoxycarbonylmethyl)-1-methylpyrrolidinium bromide;
(xiv) (2R,1'S,3'S) 3-(2-cyclopentyl-2-phenyl-2-hydroxyacetoxy)-1-(methoxycarbonylmethyl)-1-methylpyrrolidinium bromide;
(xv) (2R,1'R,3'R) 3-(2-cyclopentyl-2-phenyl-2-hydroxyacetoxy)-1-(methoxycarbonylmethyl)-1-methylpyrrolidinium bromide; and
(xvi) (2R,1'S,3'R) 3-(2-cyclopentyl-2-phenyl-2-hydroxyacetoxy)-1-(methoxycarbonylmethyl)-1-methylpyrrolidinium bromide.

Various methods of making the instant compounds are described in the art.

A compound as defined herein is of use as a pharmaceutical agent because of its anticholinergic activity. An anticholinergically effective amount of such an agent inhibits the effect of acetycholine by blocking its binding to muscarinic cholinergic receptors at neuroeffector sites. Subjects in need of a method of eliciting an anticholinergic response are those suffering from conditions which respond to treatment with an anticholinergic agent, including subjects suffering from excessive sweating or hyperhidrosis.

The compound as defined herein may be used on its own or combined with other inactive or active substances according to the description. These include, in particular, antiperspirant active substances such as aluminum chloride, aluminum chlorhydrate, or the like.

Whether or not the compound as described herein is used in conjunction with other active substances as described above, it is typically administered in the form of a pharmaceutical composition comprising an anticholinergically effective amount of the compound and a non-toxic pharmaceutically acceptable carrier therefor. Pharmaceutically acceptable carriers, or diluents, are well-known in the art. The carriers may be any inert material, organic or inorganic, suitable for administration, such as: water, alcohols, gelatin, gum arabic, lactose, microcrystalline cellulose, starch, sodium starch glycolate, calcium hydrogen phosphate, magnesium stearate, talcum, colloidal silicon dioxide, and the like.

Such compositions may also contain other pharmaceutically active agents, as noted above, and/or conventional additives such as solvents, stabilizers, wetting agents, emulsifiers, buffers, binders, disintegrants, fragrances, lubricants, glidants, antiadherents, propellants, and the like. The carrier, e.g., non-active ingredient, can be just (sterile) water with the pH adjusted to where the active pharmaceutical agent is hydrosoluble. It is preferred that the pH be at or near 6.

Alternatively and preferably, the non-active carrier agent should be physiological saline with the pH adjusted appropriately. Where the compound is slightly, moderately, or highly water-insoluble, non-toxic, pharmaceutically acceptable organic solvents or co-solvents can be used.

For example, an alcohol, such as isopropyl alcohol, ethanol, or the like can be used alone or as a cosolvent with water.

The compound as defined herein can be administered in any suitable way in accordance with the description. The compound can be made up in solid, semi-solid, or liquid form, such as powders, solutions, lotions, creams, gels, semi-solid sticks, foams, sprays, aerosols, solutions, suspensions or emulsions, and the like.

The compound as defined herein can be brought into suitable dosage forms, such as compositions for administration to a subject, preferably by topical administration, in accordance with accepted pharmaceutical procedures. The route of administration and thus the dosage form will be chosen in light of the condition to be treated with the instant anticholinergic agents. By way of illustration only, for treating hyperhydrosis, a topical preparation formulated as an antiperspirant stick, gel, spray, cream, solution, foam or the like would be preferred.

The compounds as defined herein may be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable topical excipients include alcohols, aloe vera gel, allantoin, glycerin, vitamin A and E oils, mineral oil, PPG2, myristyl propionate, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions herein can be formulated so as to provide quick, sustained or delayed release of the active ingredient after administration to the patient by employing procedures known in the art.

The composition may additionally contain one or more optional additives such as colorants, perfumes, or the like. In practice, each of these optional additives should be both miscible and compatible with the compound. Compatible additives are those that do not prevent the use of the compound in the manner described herein.

Other suitable formulations for use herein can be found in Remington's Pharmaceutical Sciences.

For purposes of illustration, liquid formulation dosages are expressed based on a percent solution (g/100 ml) or percent concentration (w/v). For solid formulation dosages, the percent concentration can be expressed as mg/mg, or w/w concentrations. A person of ordinary skill in the art would readily understand the percent concentration in the context of the type of formulation described.

In general, a therapeutically effective or anticholinergically effective amount of a compound as defined herein is from about 0.1% solution (1 µg/ml) to about 100% solution (1,000 µg/ml). Preferably, the topical composition dose is from about 1% concentration to about 25% concentration, and is most preferred using approximately 0.5 to about 1.0 ml of a composition comprising about 5% of the soft anticholinergic ester per treated area. The exact dosage of a compound as defined herein can vary depending on its potency, the mode of administration, the age and weight of the subject and the severity of the condition to be treated. The daily dosage may be administered singly or multiply one to four times daily. The compound as defined herein is unexpectedly potent for once-a day administration and exhibits higher than expected potency or activity when administered prior to bedtime.

The administration prior to bedtime does not imply at night or a particular hour or time of day; rather, before or prior to bedtime means that the composition is preferably administered, generally within about 1-2 hours prior to a person's normal rest or sleep (typically 4 to 10-hours) period. This dosage administration time was discovered to provide a preferred response or activity of the active compounds as described herein.

While not intending to be limiting, it is currently believed that administration prior to bedtime can facilitate excellent absorbance or penetration of the compound into the dermal layer, where binding to muscarinic receptors may be optimized. In addition, the natural biorhythm of subjects can allow for reduced sweating at this time of day or during sleep cycles, which also can improve the absorbance or action of the subject compounds, and the resulting response of reduced sweating during the periods of activity the following day.

More specifically, it is currently demonstrated that administration of the same or similar concentration of one or more of the subject compounds in a composition can provide a substantially identical or similar clinical (sweat reduction) response in a subject, as compared to administration of a composition containing the same concentration of glycopyrrolate. Thus, the results of this discovery are surprising in view of previously published mydriatic studies which suggested that the subject compounds in a composition were required to be present in concentration from 5 times to 10 times the concentration of a glycopyrrolate composition exhibiting a similar or substantially identical clinical response.

In addition, administration of a second dose, following the sleep cycle, within about 6-10 hours following the dose that preceded the sleep cycle, can also be a preferred method of administration or dosing regimen.

The topical dosage form for treating hyperhidrosis can be a liquid solution, semi-solid, or solid. Solutions are prepared in the usual way, e.g. with the addition of isotonic agents, preservatives such as p-hydroxybenzoates, or stabilizers such as alkali metal salts of ethylenediamine tetraacetic acid, optionally using emulsifiers and/or dispersants, while if water is used as the diluent, for example, organic solvents may optionally be used as solvating agents or dissolving aids, and transferred into vials or ampules or bottles.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulfite liquors, methylcellulose, starch and polyvinylpyrrolidone) and lubricants (e.g. magnesium stearate, talc, stearic acid and sodium lauryl sulphate).

Other compositions as described herein can be conveniently formulated using known techniques.

Example 1

An experiment can be conducted to demonstrate that activity of a compound as defined herein for use in treating hyperhidrosis is unexpectedly comparable to the activity of glycopyrrolate at equivalent doses.

Comparative Sweat Reduction in Axillary Area

A 4% solution of a soft-glycopyrrolate (e.g. ethyl or methyl ester) in 70% ethanol (Solution 1) is prepared.

A 4% solution of glycopyrrolate in 70% ethanol (Solution 2) is prepared.

Baseline sweat production assessment will be determined during 4 consecutive periods of 5 minutes (min) each under sweat stimulation conditions (92 F, 60% humidity) on day 1. Mean sweat production will be calculated and considered the baseline-5 min sweat quantity.

Reduction of sweat production can be quantitated as follows:

0.5 mL of Solution 1 applied to axillary area at bedtime on Day 1. On Day 2, approximately 8 hours after Solution 1 application, under sweat stimulation conditions (92 F, 60% humidity) and approximately at the same time of the day as baseline assessments, post-treatment sweat production will be measured during 4 consecutive periods of 5 min each. Mean sweat production will be calculated and considered the Solution 1 post-treatment 5 min sweat quantity.

Following a wash-out (no administration of the compound or composition) period of at least 7 days, the same procedure as described above will be repeated with Solution 2.

Percent change from baseline will be determined for Solution 1 and Solution 2. Statistical analysis will be conducted to estimate if the change from baseline is significant for Solution 1 and Solution 2, and whether the amount of sweat reduction is statistically similar between Solution 1 and Solution 2.

Example 2

A 5% solution of compound (v), i.e. (2R,3'R) 3-(2-cyclopentyl-2-phenyl-2-hydroxyacetoxy)-1-(methoxycarbonylmethyl)-1-ethylpyrrolidinium bromide, was prepared in 70% ethanol and tested on a human subject for its efficacy in reducing sweating.

Axillary sweat production was measured by gravimetric method: a filter paper is weighed, then place in the axilla for a 5-minute period, then re-weighed to determine the amount (weight) of sweat produced during that period. The difference in weight (dry weight) from end weight of the filter paper is determined as the sweat production for that period.

Four independent assessments are made for 5 minutes (min) each (to reduce variability) and the mean is estimated.

The baseline is the average of a total of 8 assessments of periods of 5 min each (measured in 2 days, 4 assessments each day) without treatment with the active compound.

Four once a day doses of 0.5 mL of the 5% soft-glycopyrrolate compound solution were administered to right axilla. Left axilla received only 70% ethyl alcohol solution, as control.

Post treatment assessments were conducted 8 hours after doses 2, 3, and 4, and represent the average of 4 assessments of periods of 5 min each.

The results of the experiment showed more than 50% reduction of sweat production in the soft-glycopyrrolate treated axilla compared to baseline (prior to treatment) and demonstrated efficacy for up to about 24 hours, providing the evidence of the ability of soft-glycopyrrolate compounds to elicit a clinically meaningful sweat reduction effect when applied topically. The vehicle treated axilla did not show any evidence of sweat reduction during treatment when compared with its baseline values.

The Table, below, summarizes the results.

| Percent Change from Baseline in sweat production* | | |
|---|---|---|
|  | Active (Right axilla) | Vehicle (Left axilla) |
| 8 hours After 2nd Dose | −50% | +6% |
| 8 hours After 3rd Dose | −50% | +20% |
| 8 hours After 4th Dose | −56% | +6% |
| Average for the entire treatment period. | −52% | +11% |

The percentage change from baseline was calculated from the comparison of the average sweat production at each time-point versus the baseline value for the corresponding axilla, according to the following formula:

Percent change from baseline $(PCB)=(RB/RTx)/RB\times 100$, or $PCB=(LB/LTx)/LB\times 100$, respectively, where:

RB=Average of Right axilla Baseline sweat production in a 5 min period

RTx=Average of Right axilla after (2nd or 3rd or 4th dose) Treatment sweat production in a 5 min period LB=Average of Left axilla Baseline sweat production in a 5 min period LTx=Average of Left axilla after (2 or 3 or 4 dose) Treatment sweat production in a 5 min period.

The topical application of the product was well tolerated, and did not elicit any local or systemic adverse reaction. Particularly no systemic anticholinergic effects were observed.

The observation at 32 hours after last dose (4$^{th}$ dose) indicated persistence of activity of the soft-glycopyrrolate with an average of 37% sweat reduction for the right axilla, when compared with its baseline values.

These results are indicative of surprisingly high biological activity of the soft-glycopyrrolates in reducing sweat production when applied topically, beyond what would be expected from previous pharmacodynamic anticholinergic assessments such as the mydriatic test in rabbits with these molecules.

These results are also indirectly indicative of the ability of the soft-glycopyrrolate compounds to penetrate the skin in concentration sufficient to elicit a biological effect (e.g. reduction of sweat production), when administered in a topical formulation, and the ability of the soft-glycopyrrolate compounds to bind to sweat glands' muscarinic receptors in a mammal.

In previous mydriatic studies, the compounds were found to be short-acting, whereas these particular studies surprisingly showed the subject compounds or compositions to be long-acting. These previous pharmacodynamic studies indicate that concentrations of soft-glycopyrrolate needed to achieve similar in vivo pharmacodynamic anticholinergic response were 5 times to 10 times higher than the concentration of glycopyrrolate. In this test, a 5% concentration of the soft-glycopyrrolate formulation elicited substantially similar sweat reduction (e.g. more than 50%) as compared to that previously reported for 4% glycopyrrolate solutions (See, for example, US Publication No. 2010/0276329).

While this description has been couched in terms of various preferred or exemplary embodiments, the skilled artisan will appreciate that various modifications, substitutions, omissions and changes may be made without departing from the spirit thereof. Accordingly, it is intended that the scope of the foregoing be limited only by the broadest statements herein and by the scope of the following claims, including equivalents thereof.

The invention claimed is:

1. A method of treating hyperhidrosis in a mammalian subject, said method comprising topically administering a composition comprising a pharmaceutically acceptable vehicle and from about 1.0% to about 25% of a compound having the formula:

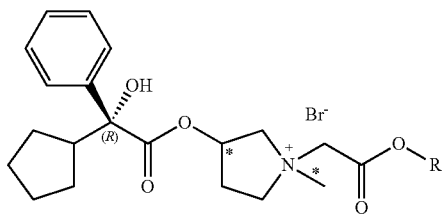

wherein R is methyl or ethyl, said compound having the R stereoisomeric configuration at the 2 position and the R, S, or RS steroisomeric configuration at the 1' and 3' position, or being a mixture thereof; to skin of an area of a mammalian subject suffering from hyperhidosis, and such that sweat production is reduced by an amount substantially equivalent to an amount that sweat production is reduced as compared to untreated, baseline conditions, following administration of a composition comprising the same concentration of glycopyrrolate, and with an improved safety profile compared to topical glycopyrrolate, and wherein the method has one or more of the following features:
  a) the subject is a human;
  b) compared to untreated, baseline conditions, sweat production is reduced by about 25% to about 99%;
  c) the composition is formulated as a solid or semi-solid, powder, gel, cream, lotion, foam, solution, suspension or emulsion;
  d) sweat production is reduced from about 8 hours to about 24 hours;
  e) the composition is applied to skin of the subject at a superficial anatomic area selected from a hand palm area, a foot plantar area, a groin area, an axilla area or a facial area.

2. The method according to claim 1, having one or more of the following features:
  a) sweat production is reduced by about 30% to about 75%;
  b) the composition is formulated as a solid or semi-solid, powder, gel, cream, lotion, foam, solution, suspension or emulsion comprising from about 2% to about 10% of said compound;
  c) sweat production is reduced from about 8 hours to about 12 hours.

3. The method according to claim 1, having one or more of the following features:
  a) sweat production is reduced from about 45% to about 60%;
  b) the composition is formulated as a 5% solution of the compound in 70% ethanol.

4. The method according to claim 1 wherein sweat production is reduced by about 50%.

5. The method according to claim 1, wherein the compound is selected from the group consisting of:
  (i) 3-(2-cyclopentyl-2-phenyl-2-hydroxyacetoxy)-1-(methoxycarbonylmethyl)-1-methylpyrrolidinium bromide;
  (ii) 3-(2-cyclopentyl-2-phenyl-2-hydroxyacetoxy)-1-(ethoxycarbonylmethyl)-1-methylpyrrolidinium bromide;
  (iii) (2R) 3-(2-cyclopentyl-2-phenyl-2-hydroxyacetoxy)-1-(methoxycarbonylmethyl)-1-methylpyrrolidinium bromide;
  (iv) (2R) 3-(2-cyclopentyl-2-phenyl-2-hydroxyacetoxy)-1-(ethoxycarbonylmethyl)-1-methylpyrrolidinium bromide;
  (v) (2R,3'R) 3-(2-cyclopentyl-2-phenyl-2-hydroxyacetoxy)-1-(methoxycarbonylmethyl)-1-methylpyrrolidinium bromide;
  (vi) (2R,3'S) 3-(2-cyclopentyl-2-phenyl-2-hydroxyacetoxy)-1-(methoxycarbonylmethyl)-1-methylpyrrolidinium bromide;
  (vii) (2R,3'R) 3-(2-cyclopentyl-2-phenyl-2-hydroxyacetoxy)-1-(ethoxycarbonylmethyl)-1-methylpyrrolidinium bromide;
  (viii) (2R,3'S) 3-(2-cyclopentyl-2-phenyl-2-hydroxyacetoxy)-1-(ethoxycarbonylmethyl)-1-methylpyrrolidinium bromide;
  (ix) (2R,1'R,3'S) 3-(2-cyclopentyl-2-phenyl-2-hydroxyacetoxy)-1-(ethoxycarbonylmethyl)-1-methylpyrrolidinium bromide;
  (x) (2R,1'S,3'S) 3-(2-cyclopentyl-2-phenyl-2-hydroxyacetoxy)-1-(ethoxycarbonylmethyl)-1-methylpyrrolidinium bromide;
  (xi) (2R,1'R,3'R) 3-(2-cyclopentyl-2-phenyl-2-hydroxyacetoxy)-1-(ethoxycarbonylmethyl)-1-methylpyrrolidinium bromide;
  (xii) (2R,1'S,3'R) 3-(2-cyclopentyl-2-phenyl-2-hydroxyacetoxy)-1-(ethoxycarbonylmethyl)-1-methylpyrrolidinium bromide;
  (xiii) (2R,1'R,3'S) 3-(2-cyclopentyl-2-phenyl-2-hydroxyacetoxy)-1-(methoxycarbonylmethyl)-1-methylpyrrolidinium bromide;
  (xiv) (2R,1'S,3'S) 3-(2-cyclopentyl-2-phenyl-2-hydroxyacetoxy)-1-(methoxycarbonylmethyl)-1-methylpyrrolidinium bromide;
  (xv) (2R,1'R,3'R) 3-(2-cyclopentyl-2-phenyl-2-hydroxyacetoxy)-1-(methoxycarbonylmethyl)-1-methylpyrrolidinium bromide; and
  (xvi) (2R,1'S,3'R) 3-(2-cyclopentyl-2-phenyl-2-hydroxyacetoxy)-1-(methoxycarbonylmethyl)-1-methylpyrrolidinium bromide.

6. The method according to claim 1, wherein the composition has two or more of the following features:
  a) the composition is formulated as a solid or semi-solid, powder, gel, cream, lotion, foam, solution, suspension or emulsion comprising from about 2% to about 10% of said compound;
  b) the composition comprises an about 5% solution of the compound in 70% ethanol;
  c) the composition comprises a compound wherein R is methyl.

7. A method of dosing a subject suffering from hyperhidrosis, said method of dosing comprising administering, before bedtime, a composition comprising a pharmaceutically acceptable vehicle and from about 1.0% to about 25% of a compound having the formula:

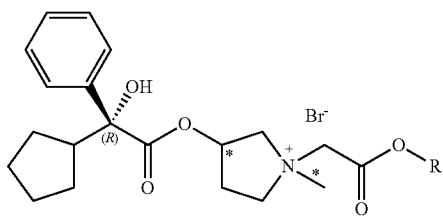

wherein R is methyl or ethyl, said compound having the R stereoisomeric configuration at the 2 position and the R, S, or RS steroisomeric configuration at the 1' and 3' position, or being a mixture thereof; to skin of an area of a subject suffering from hyperhidrosis such that sweat production is reduced by an amount substantially equivalent to an amount that sweat production is reduced as compared to untreated, baseline conditions, following administration of a composition comprising the same concentration of glycopyrrolate, and with an improved safety profile compared to topical glycopyrrolate, and wherein the method has one or more of the following features:
  a) the subject is a human;
  b) compared to untreated, baseline conditions, sweat production is reduced by about 25% to about 99%;
  c) the composition is formulated as a solid or semi-solid, powder, gel, cream, lotion, foam, solution, suspension or emulsion;

d) sweat production is reduced from about 8 hours to about 24 hours;
e) the composition is applied to skin of the subject at a superficial anatomic area selected from a hand palm area, a foot plantar area, a groin area, an axilla area or a facial area.

8. The method according to claim 7, having one or more of the following features:
   a) sweat production is reduced by about 30% to about 75%;
   b) the composition is formulated as a solid or semi-solid, powder, gel, cream, lotion, foam, solution, suspension or emulsion comprising from about 2% to about 10% of said compound;
   c) sweat production is reduced from about 8 hours to about 12 hours.

9. The method according to claim 7, having one or more of the following features:
   a) sweat production is reduced from about 45% to about 60%;
   b) the composition is formulated as a 5% solution of the compound in 70% ethanol.

10. The method according to claim 7, wherein sweat production is reduced by about 50%.

11. The method according to claim 7, wherein the compound is selected from the group consisting of:
   (i) 3-(2-cyclopentyl-2-phenyl-2-hydroxyacetoxy)-1-(methoxycarbonylmethyl)-1-methylpyrrolidinium bromide;
   (ii) 3-(2-cyclopentyl-2-phenyl-2-hydroxyacetoxy)-1-(ethoxycarbonylmethyl)-1-methylpyrrolidinium bromide;
   (iii) (2R) 3-(2-cyclopentyl-2-phenyl-2-hydroxyacetoxy)-1-(methoxycarbonylmethyl)-1-methylpyrrolidinium bromide;
   (iv) (2R) 3-(2-cyclopentyl-2-phenyl-2-hydroxyacetoxy)-1-(ethoxycarbonylmethyl)-1-methylpyrrolidinium bromide;
   (v) (2R,3'R) 3-(2-cyclopentyl-2-phenyl-2-hydroxyacetoxy)-1-(methoxycarbonylmethyl)-1-methylpyrrolidinium bromide;
   (vi) (2R,3'S) 3-(2-cyclopentyl-2-phenyl-2-hydroxyacetoxy)-1-(methoxycarbonylmethyl)-1-methylpyrrolidinium bromide;
   (vii) (2R,3'R) 3-(2-cyclopentyl-2-phenyl-2-hydroxyacetoxy)-1-(ethoxycarbonylmethyl)-1-methylpyrrolidinium bromide;
   (viii) (2R,3'S) 3-(2-cyclopentyl-2-phenyl-2-hydroxyacetoxy)-1-(ethoxycarbonylmethyl)-1-methylpyrrolidinium bromide;
   (ix) (2R,1'R,3'S) 3-(2-cyclopentyl-2-phenyl-2-hydroxyacetoxy)-1-(ethoxycarbonylmethyl)-1-methylpyrrolidinium bromide;
   (x) (2R,1'S,3'S) 3-(2-cyclopentyl-2-phenyl-2-hydroxyacetoxy)-1-(ethoxycarbonylmethyl)-1-methylpyrrolidinium bromide;
   (xi) (2R,1'R,3'R) 3-(2-cyclopentyl-2-phenyl-2-hydroxyacetoxy)-1-(ethoxycarbonylmethyl)-1-methylpyrrolidinium bromide;
   (xii) (2R,1'S,3'R) 3-(2-cyclopentyl-2-phenyl-2-hydroxyacetoxy)-1-(ethoxycarbonylmethyl)-1-methylpyrrolidinium bromide;
   (xiii) (2R,1'R,3'S) 3-(2-cyclopentyl-2-phenyl-2-hydroxyacetoxy)-1-(methoxycarbonylmethyl)-1-methylpyrrolidinium bromide;
   (xiv) (2R,1'S,3'S) 3-(2-cyclopentyl-2-phenyl-2-hydroxyacetoxy)-1-(methoxycarbonylmethyl)-1-methylpyrrolidinium bromide;
   (xv) (2R,1'R,3'R) 3-(2-cyclopentyl-2-phenyl-2-hydroxyacetoxy)-1-(methoxycarbonylmethyl)-1-methylpyrrolidinium bromide; and
   (xvi) (2R,1'S,3'R) 3-(2-cyclopentyl-2-phenyl-2-hydroxyacetoxy)-1-(methoxycarbonylmethyl)-1-methylpyrrolidinium bromide.

12. The method according to claim 7, wherein the composition has two or more of the following features:
   a) the composition is formulated as a solid or semi-solid, powder, gel, cream, lotion, foam, solution, suspension or emulsion comprising from about 2% to about 10% of said compound;
   b) the composition comprises an about 5% solution of the compound in 70% ethanol;
   c) the composition comprises a compound wherein R is methyl.

13. The method according to claim 1, wherein R in the compound is methyl.

14. The method according to claim 1, wherein R in the compound is ethyl.

15. The method according to claim 2, wherein R in the compound is methyl.

16. The method according to claim 2, wherein R in the compound is ethyl.

17. The method according to claim 7, wherein R in the compound is methyl.

18. The method according to claim 7, wherein R in the compound is ethyl.

19. The method according to claim 8, wherein R in the compound is methyl.

20. The method according to claim 8, wherein R in the compound is ethyl.

21. The method according to claim 1, wherein the composition comprises isopropyl alcohol or ethanol alone as a solvent for the compound, or as a co-solvent with water.

22. The method according to claim 21, wherein the solvent for the compound is ethanol alone.

23. The method according to claim 21, wherein R in the compound is methyl.

24. The method according to claim 21, wherein R in the compound is ethyl.

25. The method according to claim 22, wherein R in the compound is methyl.

26. The method according to claim 22, wherein R in the compound is ethyl.

27. The method according to claim 7, wherein the composition comprises isopropyl alcohol or ethanol alone as a solvent for the compound, or as a co-solvent with water.

28. The method according to claim 27, wherein the solvent for the compound is ethanol alone.

29. The method according to claim 27, wherein R in the compound is methyl.

30. The method according to claim 27, wherein R in the compound is ethyl.

31. The method according to claim 28, wherein R in the compound is methyl.

32. The method according to claim 28, wherein R in the compound is ethyl.

* * * * *

UNITED STATES PATENT AND TRADEMARK OFFICE
CERTIFICATE OF CORRECTION

PATENT NO. : 9,895,350 B2
APPLICATION NO. : 15/200129
DATED : February 20, 2018
INVENTOR(S) : Nicholas S. Bodor et al.

It is certified that error appears in the above-identified patent and that said Letters Patent is hereby corrected as shown below:

In the Claims

Column 13, Line 41, cancel the text beginning with "5. The method according to claim 1" to and ending "(xvi) (2R,1'S,3'R) 3-(2-cyclopentyl-2-phenyl-2-hydroxyacetoxy)-1-(methoxycarbonylmethyl)-1-methylpyrrolidinium bromide." at Column 14, Line 21, and insert the following claim:
--5. The method according to claim 1, wherein the compound is selected from the group consisting of:
(iii) (2R) 3-(2-cyclopentyl-2-phenyl-2-hydroxyacetoxy)-1-(methoxycarbonylmethyl)-1-methylpyrrolidinium bromide;
(iv) (2R) 3-(2-cyclopentyl-2-phenyl-2-hydroxyacetoxy)-1-(ethoxycarbonylmethyl)-1-methylpyrrolidinium bromide;
(v) (2R,3'R) 3-(2-cyclopentyl-2-phenyl-2-hydroxyacetoxy)-1-(methoxycarbonylmethyl)-1-methylpyrrolidinium bromide;
(vi) (2R,3'S) 3-(2-cyclopentyl-2-phenyl-2-hydroxyacetoxy)-1-(methoxycarbonylmethyl)-1-methylpyrrolidinium bromide;
(vii) (2R,3'R) 3-(2-cyclopentyl-2-phenyl-2-hydroxyacetoxy)-1-(ethoxycarbonylmethyl)-1-methylpyrrolidinium bromide;
(viii) (2R,3'S) 3-(2-cyclopentyl-2-phenyl-2-hydroxyacetoxy)-1-(ethoxycarbonylmethyl)-1-methylpyrrolidinium bromide;
(ix) (2R,1'R,3'S) 3-(2-cyclopentyl-2-phenyl-2-hydroxyacetoxy)-1-(ethoxycarbonylmethyl)-1-methylpyrrolidinium bromide;
(x) (2R,1'S,3'S) 3-(2-cyclopentyl-2-phenyl-2-hydroxyacetoxy)-1-(ethoxycarbonylmethyl)-1-methylpyrrolidinium bromide;
(xi) (2R,1'R,3'R) 3-(2-cyclopentyl-2-phenyl-2-hydroxyacetoxy)-1-(ethoxycarbonylmethyl)-1-methylpyrrolidinium bromide;
(xii) (2R,1'S,3'R) 3-(2-cyclopentyl-2-phenyl-2-hydroxyacetoxy)-1-(ethoxycarbonylmethyl)-1-methylpyrrolidinium bromide;
(xiii) (2R,1'R,3'S) 3-(2-cyclopentyl-2-phenyl-2-hydroxyacetoxy)-1-(methoxycarbonylmethyl)-1-methylpyrrolidinium bromide;

Signed and Sealed this
Fourth Day of December, 2018

Andrei Iancu
*Director of the United States Patent and Trademark Office*

(xiv) (2R,1'S,3'S) 3-(2-cyclopentyl-2-phenyl-2-hydroxyacetoxy)-1-(methoxycarbonylmethyl)-1-methylpyrrolidinium bromide;

(xv) (2R,1'R,3'R) 3-(2-cyclopentyl-2-phenyl-2-hydroxyacetoxy)-1-(methoxycarbonylmethyl)-1-methylpyrrolidinium bromide; and (xvi) (2R,1'S,3'R) 3-(2-cyclopentyl-2-phenyl-2-hydroxyacetoxy)-1-(methoxycarbonylmethyl)-1-methylpyrrolidinium bromide.--

Column 15, Line 25, cancel the text beginning with "11. The method according to claim 7," to and ending "(xvi) (2R,1'S,3'R) 3-(2-cyclopentyl-2-phenyl-2-hydroxyacetoxy)-1-(methoxycarbonylmethyl)-1-methylpyrrolidinium bromide." at Column 16, Line 9, and insert the following claim:

--11. The method according to claim 7, wherein the compound is selected from the group consisting of:

(iii) (2R) 3-(2-cyclopentyl-2-phenyl-2-hydroxyacetoxy)-1-(methoxycarbonylmethyl)-1-methylpyrrolidinium bromide;

(iv) (2R) 3-(2-cyclopentyl-2-phenyl-2-hydroxyacetoxy)-1-(ethoxycarbonylmethyl)-1-methylpyrrolidinium bromide;

(v) (2R,3'R) 3-(2-cyclopentyl-2-phenyl-2-hydroxyacetoxy)-1-(methoxycarbonylmethyl)-1-methylpyrrolidinium bromide;

(vi) (2R,3'S) 3-(2-cyclopentyl-2-phenyl-2-hydroxyacetoxy)-1-(methoxycarbonylmethyl)-1-methylpyrrolidinium bromide;

(vii) (2R,3'R) 3-(2-cyclopentyl-2-phenyl-2-hydroxyacetoxy)-1-(ethoxycarbonylmethyl)-1-methylpyrrolidinium bromide;

(viii) (2R,3'S) 3-(2-cyclopentyl-2-phenyl-2-hydroxyacetoxy)-1-(ethoxycarbonylmethyl)-1-methylpyrrolidinium bromide;

(ix) (2R,1'R,3'S) 3-(2-cyclopentyl-2-phenyl-2-hydroxyacetoxy)-1-(ethoxycarbonylmethyl)-1-methylpyrrolidinium bromide;

(x) (2R,1'S,3'S) 3-(2-cyclopentyl-2-phenyl-2-hydroxyacetoxy)-1-(ethoxycarbonylmethyl)-1-methylpyrrolidinium bromide;

(xi) (2R,1'R,3'R) 3-(2-cyclopentyl-2-phenyl-2-hydroxyacetoxy)-1-(ethoxycarbonylmethyl)-1-methylpyrrolidinium bromide;

(xii) (2R,1'S,3'R) 3-(2-cyclopentyl-2-phenyl-2-hydroxyacetoxy)-1-(ethoxycarbonylmethyl)-1-methylpyrrolidinium bromide;

(xiii) (2R,1'R,3'S) 3-(2-cyclopentyl-2-phenyl-2-hydroxyacetoxy)-1-(methoxycarbonylmethyl)-1-methylpyrrolidinium bromide;

(xiv) (2R,1'S,3'S) 3-(2-cyclopentyl-2-phenyl-2-hydroxyacetoxy)-1-(methoxycarbonylmethyl)-1-methylpyrrolidinium bromide;

(xv) (2R,1'R,3'R) 3-(2-cyclopentyl-2-phenyl-2-hydroxyacetoxy)-1-(methoxycarbonylmethyl)-1-methylpyrrolidinium bromide; and (xvi) (2R,1'S,3'R) 3-(2-cyclopentyl-2-phenyl-2-hydroxyacetoxy)-1-(methoxycarbonylmethyl)-1-methylpyrrolidinium bromide.--